United States Patent
O'Sullivan et al.

(10) Patent No.: US 8,013,167 B1
(45) Date of Patent: Sep. 6, 2011

(54) PROCESS FOR THE PREPARATION OF 2-CHLORO-5-CHLOROMETHYL-THIAZOLE

(75) Inventors: Anthony Cornelius O'Sullivan, Basel (CH); Laurenz Gsell, Basel (CH); Rudolf Naef, Lupsingen (CH); Marcel Senn, Blonay (CH); Thomas Pitterna, Basel (CH); David John Wadsworth, Bättwil (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 219 days.

(21) Appl. No.: 09/091,333

(22) PCT Filed: Dec. 12, 1996

(86) PCT No.: PCT/EP96/05564
§ 371 (c)(1),
(2), (4) Date: Oct. 26, 1998

(87) PCT Pub. No.: WO97/23469
PCT Pub. Date: Jul. 3, 1997

(30) Foreign Application Priority Data

Dec. 21, 1995 (CH) .................................... 3636/95

(51) Int. Cl.
*C07D 277/32* (2006.01)
(52) U.S. Cl. ........................................................ 548/202
(58) Field of Classification Search .................. 548/202
See application file for complete search history.

(56) References Cited

U.S. PATENT DOCUMENTS 5,679,769 A * 10/1997 Danishefsky et al. ........ 530/322
5,679,796 A * 10/1997 Kraatz ........................... 548/202

FOREIGN PATENT DOCUMENTS

EP 0 446 913 9/1991

* cited by examiner

*Primary Examiner* — Rei-tsang Shiao
(74) *Attorney, Agent, or Firm* — James Cueva

(57) ABSTRACT

The invention relates to a process for the preparation of 2-chloro-5-chloromethyl-thiazole, which is employed as intermediate in the preparation of compounds having a pesticidal action, which process comprises reacting a compound of formula (II), in free form or in salt form, (III), (IV), (V) or (VI) with a chlorinating agent, where R and $M^+$ are as defined in claim 1; to the compounds of the formulae (III) and (IV), which are used in this process as intermediates; and to the use of, and a process for the preparation of, the compounds of formulae (III) and (IV).

10 Claims, No Drawings

PROCESS FOR THE PREPARATION OF 2-CHLORO-5-CHLOROMETHYL-THIAZOLE

This is a 371 of PCT/EP/96/05489, Dec. 7, 1996.

The invention relates to a process for preparing the known compound of the formula

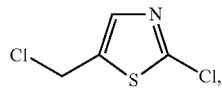

I which comprises
a) reacting the known compound of the formula

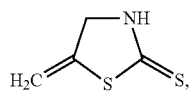

II in free form or in salt form, with a chlorinating agent, or
b) reacting a compound of the formula

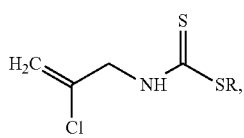

III which is known or can be prepared by methods known per se and in which R is $C_1$-$C_6$alkyl, $C_3$-$C_6$cycloalkyl or an unsubstituted or mono- to pentasubstituted aryl or aryl-C group, where the substituents are selected from the group consisting of halogen and $C_1$-$C_4$alkyl, with a chlorinating agent, or
c) reacting the compound of the formula

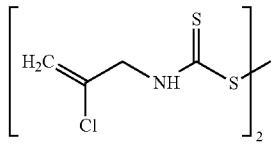

IV with a chlorinating agent, or
d) reacting a compound of the formula

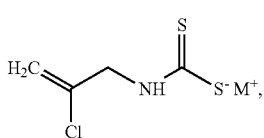

V which is known or can be prepared by methods known per se and in which $M^+$ is an alkali metal ion, one equivalent of an alkaline earth metal ion or is a nonalkylated ammonium ion or an ammonium ion which is alkylated with from one to four identical or different alkyl radicals, and is preferably a potassium ion or, in particular, a sodium ion, with a chlorinating agent, or e) reacting the compound of the formula

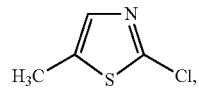

VI which is known, in the presence or absence of a free-radical catalyst, with a chlorinating agent, or f1) first reacting the compound of the formula II or the compound 2-mercapto-5-methyl-thiazole, in each case in free form or in salt form, with a chlorinating agent, and f2) subjecting the compound of the formula VI which is obtainable in this way to further reaction, with or without isolating it, with a chlorinating agent in accordance with variant e), or g) subjecting a compound of the formula V either
g1.1) first to treatment with a base and
g1.2) the compound of the formula II thus obtainable, in free form or in salt form, with or without isolating it, to further reaction with a chlorinating agent in accordance with variant a) or in accordance with variant f1/f2), or g2.1) first to reaction with a compound of the formula RX, which is known or can be prepared by methods known per se and in which R is as defined for the formula III and X is a leaving group, and g2.2) the compound of the formula III thus obtainable, with or without isolating it, to further reaction with a chlorinating agent in accordance with variant b), or g3.1) first of all to reaction with an oxidizing agent, in the presence or absence of a base, and g3.2) the compound of the formula IV thus obtainable, with or without isolating it, to further reaction with a chlorinating agent in accordance with variant c), or h1) reacting the compound of the formula

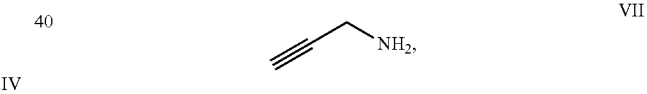

VII which is known, first of all with carbon disulfide, in the presence or absence of a base, and h2) further reacting the compound of the formula II thus obtainable, in free form or in salt form, with or without isolating it, with a chlorinating agent in accordance with variant a) or in accordance with variant f1/f2);

to the compounds of the formulae III and IV, which are employed in this process as intermediates; and to the use of, and a process for the preparation of, the compounds of the formulae III and IV.

2-Chloro-5-chloromethylthiazole I is an important intermediate in the preparation of compounds having a pesticidal action, as are described, for example, in EP-A-0 192 060.

Unless defined otherwise, the general terms used above and below have the following meanings.

Halogen—both as a group on its own and as a structural element of other groups and compounds, such as of haloalkyl and halocyclopropyl—is fluorine, chlorine, bromine or iodine, especially fluorine, chlorine or bromine, in particular fluorine or chlorine, and most especially chlorine.

Compounds and groups containing carbon include, unless defined otherwise, in each case from 1 up to and including 6, preferably from 1 up to and including 3, and in particular 1 or 2, carbon atoms.

Cycloalkyl is cyclopropyl, cyclobutyl, cyclopentyl or cyclohexyl, preferably cyclopropyl.

Alkyl—both as a group per se and as a structural element of other groups and compounds, such as of phenylalkyl and haloalkyl—is (always taking into account the particular number of carbon atoms in the relevant group or compound) either straight-chain, i.e. methyl, ethyl, propyl, butyl, pentyl or hexyl, or branched, e.g. isopropyl, isobutyl, sec-butyl, tert-butyl, isopentyl, neopentyl or isohexyl.

Aryl is phenyl oder naphthyl, especially phenyl.

Depending on requirements, the reactions described above and below are carried out in the presence or absence of an appropriate solvent or diluent or mixture thereof, with cooling, at room temperature or heating, for example in a temperature range from about −80° C. to the boiling temperature of the reaction medium, preferably from about −60° C. to about +200° C., in a closed vessel under atmospheric, elevated or reduced pressure, under an inert gas atmosphere and/or under hydrogen-free conditions. Particularly advantageous reaction conditions are described below and can be inferred in particular from the Preparation Examples.

Variant a):

Examples of suitable chlorinating agents are elemental chlorine, Javelle water (NaHClO), N-chlorosuccinimide, phosphorus trichloride, phosphorus pentachloride, sulfuryl chloride, thionyl chloride or mixtures of two or more of these compounds, preferably elemental chlorine, sulfuryl chloride or a mixture of these two compounds, particularly preferably sulfuryl chloride.

The reactants can be reacted with one another without adding a solvent or diluent. However, the addition of a solvent or diluent or mixture thereof may also be advantageous, its amount not being critical. Examples of such solvents or diluents are: water; alcohols, such as methanol, ethanol, propanol, isopropanol, butanol, ethylene glycol or glycerol, aromatic, aliphatic and alicyclic hydrocarbons and halogenated hydrocarbons, such as benzene, toluene, xylene, mesitylene, tetralin, chlorobenzene, dichlorobenzene, bromobenzene, petroleum ether, hexane, cyclohexane, dichloromethane, trichloromethane, tetrachloromethane, dichloroethane, trichloroethene or tetrachloroethene; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; amides, such as N,N-dimethylformamide, N,N-diethylformamide, N,N-dimethylacetamide, N-methylpyrrolidone or hexamethylphosphoramide; nitriles, such as acetonitrile or propionitrile; and sulfoxides, such as dimethyl sulfoxide. If reaction is carried out in the presence of an organic acid, then it is also possible for acids employed in excess, for example strong organic carboxylic acids, such as unsubstituted or substituted—for example by halogen-$C_1$-$C_4$alkanecarboxylic acids, examples being formic acid, acetic acid or propionic acid, to be used as solvent or diluent. The reaction is preferably carried out in the presence of a halogenated hydrocarbon, especially in dichloromethane.

Reaction takes place advantageously in a temperature range from about −20° C. to about +180° C., preferably from about 0° C. to about +80° C., and in many cases in the range between room temperature and the reflux temperature of the reaction mixture.

In a preferred embodiment of variant a) a compound II is reacted at from 0 to 40°, preferably from 10 to 15°, with a chlorinating agent, preferably sulfuryl chloride.

Reaction takes place preferably at atmospheric pressure.

The reaction time is not critical; a reaction period of from 0.1 to 48 hours is preferred, especially from 0.5 to 4 hours.

The product is isolated by conventional methods, for example filtration, crystallization, distillation or chromatography, or by any appropriate combination of these methods.

The yields obtained are generally good. It is possible to attain a yield of about 70% of the theoretical yield.

Preferred conditions for the reaction are described in Examples H1 to H3.

Variant b):

Examples of suitable chlorinating agents are those indicated under variant a).

The reactants can be reacted with one another as they are, i.e. without the addition of a solvent or diluent, for example in the melt. However, in most cases the addition of a solvent or diluent or mixture thereof is advantageous. Examples of suitable solvents and diluents are those indicated under variant a).

Reaction takes place advantageously in a temperature range of about −20° C. to about +180° C., preferably from about 0° C. to about +80° C., and in many cases in the range between room temperature and the reflux temperature of the reaction mixture.

In a preferred embodiment of variant b), a compound III is reacted at −10 to 40°, preferably 0°, with a chlorinating agent, preferably sulfuryl chloride.

The reaction takes place preferably at atmospheric pressure.

The reaction time is not critical; a reaction period of from 0.1 to 48 hours is preferred, especially from 1 to 24 hours.

The product is isolated by conventional methods, for example filtration, crystallization, distillation or chromatography, or by any appropriate combination of these methods.

Preferred conditions for the reaction are described in Example H4.

Variant c):

Examples of suitable chlorinating agents are those indicated under variant a).

The reactants can be reacted with one another as they are, i.e. without the addition of a solvent or diluent, for example in the melt. However, in most cases the addition of a solvent or diluent or mixture thereof is advantageous. Examples of suitable solvents and diluents are those indicated under variant a).

Reaction takes place advantageously in a temperature range of about −20° C. to about +180° C., preferably from about 0° C. to about +80° C., and in many cases in the range between room temperature and the reflux temperature of the reaction mixture.

In a preferred embodiment of variant c), a compound IV is reacted at −10 to 40°, preferably 0°, with a chlorinating agent, preferably sulfuryl chloride.

The reaction takes place preferably at atmospheric pressure.

The reaction time is not critical; a reaction period of from 0.1 to 48 hours is preferred, especially from 1 to 24 hours.

The product is isolated by conventional methods, for example filtration, crystallization, distillation or chromatography, or by any appropriate combination of these methods.

Preferred conditions for the reaction are described in Example H5.

Variant d):

Examples of suitable chlorinating agents are those indicated under variant a).

The reactants can be reacted with one another as they are, i.e. without the addition of a solvent or diluent, for example in the melt. However, in most cases the addition of a solvent or diluent or mixture thereof is advantageous. Examples of suitable solvents and diluents are those indicated under variant a).

Reaction takes place advantageously in a temperature range of about −20° C. to about +180° C., preferably from about 0° C. to about +80° C., and in many cases in the range between room temperature and the reflux temperature of the reaction mixture.

The reaction takes place preferably at atmospheric pressure.

The reaction time is not critical; a reaction period of from 0.1 to 48 hours is preferred, especially from 1 to 24 hours.

The product is isolated by conventional methods, for example filtration, crystallization, distillation or chromatography, or by any appropriate combination of these methods.

Variant e):

Examples of suitable free-radical catalysts are azobis(isobutyronitrile) or, in particular, dibenzoyl peroxide.

Examples of suitable chlorinating agents are those indicated under variant a).

The reactants can be reacted with one another as they are, i.e. without the addition of a solvent or diluent, for example in the melt. However, in most cases the addition of a solvent or diluent or mixture thereof is advantageous. Examples of suitable solvents and diluents are those indicated under variant a).

Reaction takes place advantageously in a temperature range of about −20° C. to about +180° C., preferably from about 0° C. to about +80° C., and in many cases in the range between room temperature and the reflux temperature of the reaction mixture.

In a preferred embodiment of variant e), a compound VI is reacted at 10 to 120°, preferably 80°, with a chlorinating agent, preferably N-chlorosuccinimide.

The reaction takes place preferably at atmospheric pressure.

The reaction time is not critical; a reaction period of from 0.1 to 100 hours is preferred, especially from 12 to 72 hours.

The product is isolated by conventional methods, for example filtration, crystallization, distillation or chromatography, or by any appropriate combination of these methods.

Preferred conditions for the reaction are described in Example H6.

Variant f1/f2):

Examples of suitable chlorinating agents are those indicated under variant a).

The reactants can be reacted with one another as they are, i.e. without the addition of a solvent or diluent, for example in the melt. However, in most cases the addition of a solvent or diluent or mixture thereof is advantageous. Examples of suitable solvents and diluents are those indicated under variant a).

Reaction takes place advantageously in a temperature range of about −20° C. to about +80° C., preferably from about −10° C. to about +40° C., and in many cases in the range between room temperature and the reflux temperature of the reaction mixture.

In a preferred embodiment of variant f1/f2), a compound II is initially reacted at −10 to 40°, preferably 0°, with a chlorinating agent, preferably sulfuryl chloride, to give a compound of the formula VI which then, preferably after it has been isolated, is subjected to further reaction with a further chlorinating agent, preferably N-chlorosuccinimide.

The reaction takes place preferably at atmospheric pressure.

The reaction time is not critical; a reaction period of from 0.1 to 100 hours is preferred, especially from 1 to 72 hours, preferably from 12 to 72 hours.

The product is isolated by conventional methods, for example filtration, crystallization, distillation or chromatography, or by any appropriate combination of these methods.

2-Mercapto-5-methyl-thiazole, which can be used also in its tautomeric form (2-thioxo compound), can be obtained, for example, by acid treatment of the compound of the formula II.

Preferred conditions for the reactions are described in Examples H6, H7 and H9.

Variant g1.1):

Examples of suitable bases for facilitating the reaction are alkali metal or alkaline earth metal hydroxides, hydrides, amides, alkanolates, acetates, carbonates, dialkylamides or alkylsilylamides, alkylamines, alkylenediamines, nonalkylated or N-alkylated, saturated or unsaturated cycloalkylamines, basic heterocycles, ammonium hydroxides and carbocyclic amines. Specific examples are sodium hydroxide, hydride, amide, methanolate, acetate and carbonate, potassium tert-butanolate, hydroxide, carbonate and hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,5-diazabicyclo[5.4.0]undec-5-ene (DBU).

Examples of suitable chlorinating agents are those indicated under variant a).

The reactants can be reacted with one another as they are, i.e. without the addition of a solvent or diluent, for example in the melt. However, in most cases the addition of a solvent or diluent or mixture thereof is advantageous. Examples of suitable solvents and diluents are those indicated under variant a).

Reaction takes place advantageously in a temperature range of about −20° C. to about +80° C., preferably from about −10° C. to about +40° C., and in many cases in the range between room temperature and the reflux temperature of the reaction mixture.

The reaction takes place preferably at atmospheric pressure.

The reaction time is not critical; a reaction period of from 0.1 to 100 hours is preferred, especially from 12 to 72 hours.

The product is isolated by conventional methods, for example filtration, crystallization, distillation or chromatography, or by any appropriate combination of these methods.

Variant g1.2):

Examples of suitable chlorinating agents are those indicated under variant a).

The reactants can be reacted with one another as they are, i.e. without the addition of a solvent or diluent, for example in the melt. However, in most cases the addition of a solvent or diluent or mixture thereof is advantageous. Examples of suitable solvents and diluents are those indicated under variant a).

Reaction takes place advantageously in a temperature range of about −20° C. to about +180° C., preferably from about 0° C. to about +80° C., and in many cases in the range between room temperature and the reflux temperature of the reaction mixture.

In a preferred embodiment of variant g1.2), a compound II is reacted at 0 to 40°, preferably 10 to 15°, with a chlorinating agent, preferably sulfuryl chloride.

The reaction takes place preferably at atmospheric pressure.

The reaction time is not critical; a reaction period of from 0.1 to 48 hours is preferred, especially from 0.5 to 4 hours.

The product is isolated by conventional methods, for example filtration, crystallization, distillation or chromatography, or by any appropriate combination of these methods.

Preferred conditions for the reaction are described in Examples H1 to H3, H6, H7 and H9.

Variant g2.1):

Suitable leaving groups X are, for example, hydroxyl, $C_1$-$C_8$alkoxy, halo-$C_1$-$C_8$alkoxy, $C_1$-$C_8$alkanoyloxy, mercapto, $C_1$-$C_8$alkylthio, halo-$C_1$-$C_8$alkylthio, $C_1$-$C_8$alkanesulfonyloxy, halo-$C_1$-$C_8$alkanesulfonyloxy, benzenesulfonyloxy, toluenesulfonyloxy and halogen, preferably toluenesulfonyloxy, trifluoromethanesulfonyloxy and halogen, especially halogen.

The reactants can be reacted with one another as they are, i.e. without the addition of a solvent or diluent, for example in the melt. However, in most cases the addition of a solvent or diluent or mixture thereof is advantageous. Examples of suitable solvents and diluents are those indicated under variant a).

Reaction takes place advantageously in a temperature range of about −20° C. to about +180° C., preferably from about 0° C. to about +80° C., and in many cases in the range between room temperature and the reflux temperature of the reaction mixture.

The reaction takes place preferably at atmospheric pressure.

The reaction time is not critical; a reaction period of from 0.1 to 48 hours is preferred, especially from 0.5 to 4 hours.

The product is isolated by conventional methods, for example filtration, crystallization, distillation or chromatography, or by any appropriate combination of these methods.

Variant g2.2):

Examples of suitable chlorinating agents are those indicated under variant a).

The reactants can be reacted with one another as they are, i.e. without the addition of a solvent or diluent, for example in the melt. However, in most cases the addition of a solvent or diluent or mixture thereof is advantageous. Examples of suitable solvents and diluents are those indicated under variant a).

Reaction takes place advantageously in a temperature range of about −20° C. to about +180° C., preferably from about 0° C. to about +80° C., and in many cases in the range between room temperature and the reflux temperature of the reaction mixture.

In a preferred embodiment of variant g2.2), a compound III is reacted at −10 to 40°, preferably 0°, with a chlorinating agent, preferably sulfuryl chloride.

The reaction takes place preferably at atmospheric pressure.

The reaction time is not critical; a reaction period of from 0.1 to 48 hours is preferred, especially from 1 to 24 hours.

The product is isolated by conventional methods, for example filtration, crystallization, distillation or chromatography, or by any appropriate combination of these methods.

Preferred conditions for the reaction are described in Example H4.

Variant g3.1):

Examples of suitable oxidizing agents are air, nitrogen monoxide, elemental halogens, alkali metal chlorates, inorganic peroxides, for example hydrogen peroxide, or sodium perborate, organic peroxides, for example benzoyl peroxide, or dimethyl sulfoxide, preferably elemental halogens or hydrogen peroxide, especially iodine.

Suitable bases for facilitating the reaction are, for example, of the type indicated under variant g1.1).

The reactants can be reacted with one another as they are, i.e. without the addition of a solvent or diluent, for example in the melt. However, in most cases the addition of a solvent or diluent or mixture thereof is advantageous. Examples of suitable solvents and diluents are those indicated under variant a).

Reaction takes place advantageously in a temperature range of about −20° C. to about +180° C., preferably from about 0° C. to about +80° C., and in many cases in the range between room temperature and the reflux temperature of the reaction mixture.

In a preferred embodiment of variant g3.1), a compound V is reacted at −10 to 40°, preferably 0°, with an oxidizing agent, preferably iodine.

The reaction takes place preferably at atmospheric pressure.

The reaction time is not critical; a reaction period of from 0.1 to 48 hours is preferred, especially from 0.5 to 4 hours.

The product is isolated by conventional methods, for example filtration, crystallization, distillation or chromatography, or by any appropriate combination of these methods.

Preferred conditions for the reaction are described in Example H8.

Variant g3.2):

Examples of suitable chlorinating agents are those indicated under variant a).

The reactants can be reacted with one another as they are, i.e. without the addition of a solvent or diluent, for example in the melt. However, in most cases the addition of a solvent or diluent or mixture thereof is advantageous. Examples of suitable solvents and diluents are those indicated under variant a).

Reaction takes place advantageously in a temperature range of about −20° C. to about +180° C., preferably from about 0° C. to about +80° C., and in many cases in the range between room temperature and the reflux temperature of the reaction mixture.

In a preferred embodiment of variant g3.2), a compound IV is reacted at −10 to 40°, preferably 0°, with a chlorinating agent, preferably sulfuryl chloride.

The reaction takes place preferably at atmospheric pressure.

The reaction time is not critical; a reaction period of from 0.1 to 48 hours is preferred, especially from 1 to 24 hours.

The product is isolated by conventional methods, for example filtration, crystallization, distillation or chromatography, or by any appropriate combination of these methods.

Preferred conditions for the reaction are described in Example H5.

Variant h1:

Examples of suitable bases for facilitating the reaction are those indicated under variant g1.1).

The reactants can be reacted with one another as they are, i.e. without the addition of a solvent or diluent, for example in the melt. However, in most cases the addition of a solvent or diluent or mixture thereof is advantageous. Examples of suitable solvents and diluents are those indicated under variant a).

Reaction takes place advantageously in a temperature range of about −20° C. to about +180° C., preferably from about 0° C. to about +80° C., and in many cases in the range between room temperature and the reflux temperature of the reaction mixture.

The reaction takes place preferably at atmospheric pressure.

The reaction time is not critical; a reaction period of from 0.1 to 48 hours is preferred, especially from 1 to 24 hours.

The product is isolated by conventional methods, for example filtration, crystallization, distillation or chromatography, or by any appropriate combination of these methods.

Variant h2):

Examples of suitable chlorinating agents are those indicated under variant a).

The reactants can be reacted with one another as they are, i.e. without the addition of a solvent or diluent, for example in the melt. However, in most cases the addition of a solvent or diluent or mixture thereof is advantageous. Examples of suitable solvents and diluents are those indicated under variant a).

Reaction takes place advantageously in a temperature range of about −20° C. to about +180° C., preferably from about 0° C. to about +80° C., and in many cases in the range between room temperature and the reflux temperature of the reaction mixture.

In a preferred embodiment of variant h2), a compound II is reacted at 0 to 40°, preferably 10 to 15°, with a chlorinating agent, preferably sulfuryl chloride.

The reaction takes place preferably at atmospheric pressure.

The reaction time is not critical; a reaction period of from 0.1 to 48 hours is preferred, especially from 0.5 to 4 hours.

The product is isolated by conventional methods, for example filtration, crystallization, distillation or chromatography, or by any appropriate combination of these methods.

Preferred conditions for the reaction are described in Examples H1 to H3, H6, H7 and H9.

The invention likewise provides starting materials and intermediates which are novel and which are used in accordance with the invention to prepare compound I, a process for their preparation, and their use as starting materials and intermediates for preparing the compound I; this pertains in particular to the compounds III and IV.

The invention likewise provides a process for the preparation of the compounds III and IV. The compound III can be prepared, for example, as described under variant g2.1). The compound IV can be prepared, for example, as described under variant g3.1).

The invention likewise provides for the use of the compound III or IV as an intermediate in the novel process for the preparation of the compound I.

The invention additionally provides starting materials and intermediates, in each case in free form or in salt form if applicable, which are novel and which are used in accordance with the invention for preparing compounds II, III, IV and VI and/or their salts, and to a process for their preparation, and for their use as starting materials and intermediates for preparing compounds II, III, IV and VI.

The compounds II, V, VI and VII are known or, where novel, can be prepared in analogy to known compounds.

The invention relates to all those process embodiments in which the starting material is a compound obtainable as an initial product or intermediate at any stage of the process and in which all or some of the missing steps are carried out or in which a starting material is used in the form of a derivative or salt and/or its racemates or enantiomers or, in particular, is formed under the reaction conditions.

The invention relates in particular to the processes described in Examples H1 to H9.

The examples which follow serve to illustrate the invention. They do not restrict the invention. Temperatures are given in degrees Celsius.

EXAMPLES

Example H1

2-Chloro-5-chloromethylthiazole from 5-methylenethiazolidine-2-thione (compound II)

4 g of chlorine gas are passed at 10-15° C. into a solution of 100 ml of acetic acid and 7 ml of water. Subsequently, at the same temperature, 9.2 g of 5-methylenethiazolidine-2-thione, 12 ml of 30% sodium hydroxide solution, 28 ml of water and 21 g of chlorine gas are metered in over the course of 2-3 hours. Then 100 ml of water are added to this reaction mixture, and extraction is carried out three times with 30 ml of toluene. The organic phase is dried over sodium sulfate and concentrated in vacuo at 45° C. to give the title compound in a yield of 56% (melting point: 35° C.)

Example H2

2-Chloro-5-chloromethylthiazole from 5-methylenethiazolidine-2-thione (compound II)

1.31 g of 5-methylenethiazolidine-2-thione are added in portions at 0° C., with stirring, to a solution of 5.4 g of sulfuryl chloride in 8 ml of dichloromethane and 0.72 ml of water. The reaction mixture is subsequently stirred at room temperature for 1 hour. The mixture is then adjusted to a pH of 2 with 30% sodium hydroxide solution, and the organic phase is separated off, dried over sodium sulfate and concentrated in vacuo to give the title compound in a yield of 70% (melting point: 35° C.).

Example H3

2-Chloro-5-chloromethylthiazole from 5-methylenethiazolidine-2-thione (compound II)

1 ml of water at −5° C. and then, at the same temperature over the course of 5 minutes, 1.4 g of 5-methylenethiazolidine-2-thione in five portions are added to a mixture of 13 ml of dichloromethane and 10 g of sulfuryl chloride. The reaction mixture is then diluted with 20 ml of water and 33 ml of dichloromethane, it is neutralized with about 24 ml of 30% sodium hydroxide solution, and the organic phase is separated off. The aqueous phase is subjected to extraction with 27 ml of dichloromethane, and the combined extracts are dried over sodium sulfate and concentrated in vacuo at 35° C., to give the title compound in a yield of 31% (melting point: 35° C.).

Example H4

2-Chloro-5-chloromethylthiazole from benzyl 2-chloro-2-propenyldithio-carbamate (compound III, R=benzyl)

358 mg of sulfuryl chloride are slowly added dropwise with stirring at 0° C. to a solution of 341 mg of benzyl 2-chloro-2-propenyldithiocarbamate in 0.3 ml of dichloromethane. After 18 hours the reaction mixture is concentrated in vacuo at room temperature, the residue is subjected to extraction with hexane, and the organic phase is dried over sodium sulfate and concentrated in vacuo to give the title compound (melting point: 35° C.).

Example H5

2-Chloro-5-chloromethylthiazole from compound IV 283 mg of sulfuryl chloride are slowly added dropwise with stirring at 0° C. to a solution of 135 mg of the compound IV in 0.2 ml of dichloromethane. The reaction mixture is stirred at room temperature for 18 hours and subjected to extraction with hexane, and the organic phase is dried over sodium sulfate and concentrated in vacuo to give the title compound (melting point: 35° C.).

Example H6

2-Chloro-5-chloromethylthiazole from 2-chloro-5-methylthiazole (compound VI)

5 mg of dibenzoyl peroxide in portions and then 155 mg of N-chlorosuccinimide are added at room temperature and with stirring to a solution of 124 mg of 2-chloro-5-methylthiazole in 4 ml of carbon tetrachloride. The reaction mixture is boiled under reflux for 64 hours, then a further 5 mg of dibenzoyl peroxide and 155 mg of N-chlorosuccinimide are added, and boiling is resumed for 8 hours. After cooling to room temperature, the suspension is filtered and the residue is washed with carbon tetrachloride. The organic phase is then concentrated in vacuo and the residue is purified by chromatography on silica gel with ethyl acetate/hexane (1:9), to give the title compound (melting point: 35° C.).

Example H7

2-Chloro-5-methylthiazole (compound VI) from 5-methylenethiazolidine-2-thione (compound II)

1.31 g of 5-methylenethiazolidine-2-thione are added in portions with stirring and at 0° C. to a solution of 5.4 g of sulfuryl chloride in 8 ml of dichloromethane and 0.72 ml of water. The reaction mixture is subsequently stirred at room temperature for 1 hour and then adjusted to a pH of 2 using 30% sodium hydroxide solution, and the organic phase is separated off, washed a number of times with water, dried over sodium sulfate and concentrated by evaporation, to give 2-chloro-5-methylthiazole with a boiling point of 174° C.

Example H8

Compound IV from sodium N-(2-chloro-2-propenyl)dithiocarbamate (compound V, M=sodium)

3.81 g of carbon disulfide are added with stirring and at 0° C. to a solution of 4.58 g of 2-chloroallylamine in 25 ml of 2 N sodium hydroxide solution. A solution of 6.35 g of iodine and 4.32 g of potassium iodide in a little water is added to the solution of sodium N-(2-chloro-2-propenyl)dithiocarbamate obtainable as described in the first sentence of this example. The crude, oily product is separated off and is purified by chromatography on silica gel using ethyl acetate/hexane (1:10 to 1:1), to give the compound IV.

Example H9

2-Chloro-5-methyl-thiazole (compound VI) from 2-mercapto-5-methyl-thiazole 1.35 g of 2-mercapto-5-methyl-thiazole are added in portions, with stirring and at 0°, to a solution of 5.8 g of sulfuryl chloride in 9 ml of dichloromethane and 720 mg of water. The reaction mixture is subsequently stirred at room temperature for 1 hour and then adjusted to a pH of 2 using aqueous sodium hydroxide solution (30%). The organic phase is separated off, dried over sodium sulfate and concentrated by evaporation, to give 1.99 g of 2-chloro-5-methyl-thiazole with a boiling point of 174°.

What is claimed is:

1. A process for preparing a compound of the formula

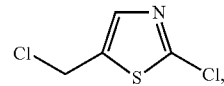

I which comprises reacting a compound of the formula

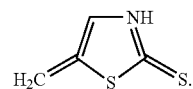

II in free form or in salt form, with a chlorinating agent.

2. A process according to claim 1, wherein the chlorinating agent is selected from the group consisting of elemental chlorine, Javelle water, N-chlorosuccinimid, phosphorus trichloride, phosphorus pentachloride, sulfuryl chloride, thionyl chloride and mixtures of two or more of these compounds.

3. A process according to claim 2, wherein the chlorinating agent is selected from the group consisting of elemental chlorine, sulfuryl chloride and a mixture of these two compounds.

4. A process according to claim 3, wherein the chlorinating agent is sulfuryl chloride.

5. A process according to claim 1, wherein the reaction is run in a solvent is selected from the group consisting of water, strong organic carboxylic acids, aromatic, aliphatic and alicyclic hydrocarbons and halogenated hydrocarbons, and mixtures of these solvents.

6. A process according to claim 5, wherein the solvent is selected from the group consisting of water, formic acid, acetic acid, propionic acid, benzene, toluene, xylene, mesitylene, tetralin, chlorobenzene, dichlorobenzene, bromobenzene, petroleum ether, hexane, cyclohexane, dichloromethane, trichloromethane, tetrachloromethane, dichloroethane, trichloroethane, tetrachloroethane, and mixtures of these solvents.

7. A process according to claim 6, wherein the solvent is a mixture of water and dichloromethane.

8. A process according to claim 7, wherein the weight ratio of dichloromethane to water is from about 5 to about 50.

9. A process according to claim 1, wherein the reaction is carried out at from about −10° C. to about +40° C.

10. A process according to claim 1, wherein the reaction period is from about 0.1 to about 4 hours.

* * * * *